(12) United States Patent
Billot et al.

(10) Patent No.: US 9,533,953 B2
(45) Date of Patent: Jan. 3, 2017

(54) METHOD OF PREPARATION OF CRYSTAL FORMS OF 4-(CYCLOPROPYLMETHOXY)-N-(3,5-DICHLORO-1-OXIDOPYRIDYN-4-YL)-5-METHOXYPYRIDINE-2-CARBOXAMIDE AND CRYSTAL FORMS THEREOF

(71) Applicant: SANOFI, Paris (FR)

(72) Inventors: Pascal Billot, Paris (FR); Didier Brige, Paris (FR); Alexandre Giuliani, Paris (FR); Hagit Elmaleh, Paris (FR); Marc-Antoine Perrin, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/647,799

(22) PCT Filed: Nov. 28, 2013

(86) PCT No.: PCT/EP2013/074972
§ 371 (c)(1),
(2) Date: May 27, 2015

(87) PCT Pub. No.: WO2014/083107
PCT Pub. Date: Jun. 5, 2014

(65) Prior Publication Data
US 2015/0322014 A1 Nov. 12, 2015

(30) Foreign Application Priority Data
Nov. 28, 2012 (EP) ................................. 12306479

(51) Int. Cl.
*C07D 213/89* (2006.01)

(52) U.S. Cl.
CPC ................................. *C07D 213/89* (2013.01)

(58) Field of Classification Search
None
See application file for complete search history.

(56) References Cited

FOREIGN PATENT DOCUMENTS

| WO | 95/04045 | * | 2/1995 |
|---|---|---|---|
| WO | WO-95/04045 A1 | | 2/1995 |

OTHER PUBLICATIONS

Written Opinion of the International Searching Authority mailed on Feb. 5, 2014, for PCT Application No. PCT/EP2013/074972, filed on Nov. 28, 2013, four pages.
Caira, M.R. (1998). "Crystalline Polymorphism of Organic Compounds," *Topics in Current Chemistry* 198:163-208.
International Search Report mailed on Feb. 5, 2014, for PCT Application No. PCT/EP2013/074972, filed on Nov. 28, 2013, three pages.

* cited by examiner

*Primary Examiner* — Karl J Puttlitz
(74) *Attorney, Agent, or Firm* — Morrison & Foerster LLP

(57) ABSTRACT

The present invention relates to a process of preparation of Crystal Forms of 4-(cyclopropylmethoxy)-N-(3,5-dichloro-1-oxidopyridin-4-yl)-5-methoxypyridine-2-carboxamide of formula (I), said Crystal Forms which are designated as Crystal Forms A to I A and their use as a medicament.

5 Claims, 15 Drawing Sheets

XRPD diagram of Form A - Diffractometer Panalytical ($\lambda_{Cu} K\alpha_1 = 1.5406$ Å)

XRPD diagram of Form A - Diffractometer Panalytical ($\lambda_{Cu}\ K\alpha_1 = 1.5406$ Å)

Form A - TGA curve

Form A - Sorption/desorption water isotherm recorded at 25°C

Figure 4: XRPD diagram of Form B - Diffractometer Panalytical ($\lambda_{Cu}\,K\alpha_1$ = 1.5406 Å)

Figure 5: XRPD diagram of Form C - Diffractometer Bruker D5000 ($\lambda_{Co}\ K\alpha_1\alpha_2 = 1.79030$ Å)

Figure 6: XRPD diagram of Form D - Diffractometer Panalytical ($\lambda_{Cu}\ K\alpha_1 = 1.5406$ Å)

Form D - TGA curve

Form D - Sorption/desorption water isotherm recorded at 25°C

Figure 9: XRPD diagram of Form E - Diffractometer Panalytical ($\lambda_{Cu}\ K\alpha_1 = 1.5406\ Å$)

Form E - TGA curve

Form E - Sorption/desorption water isotherm recorded at 25°C

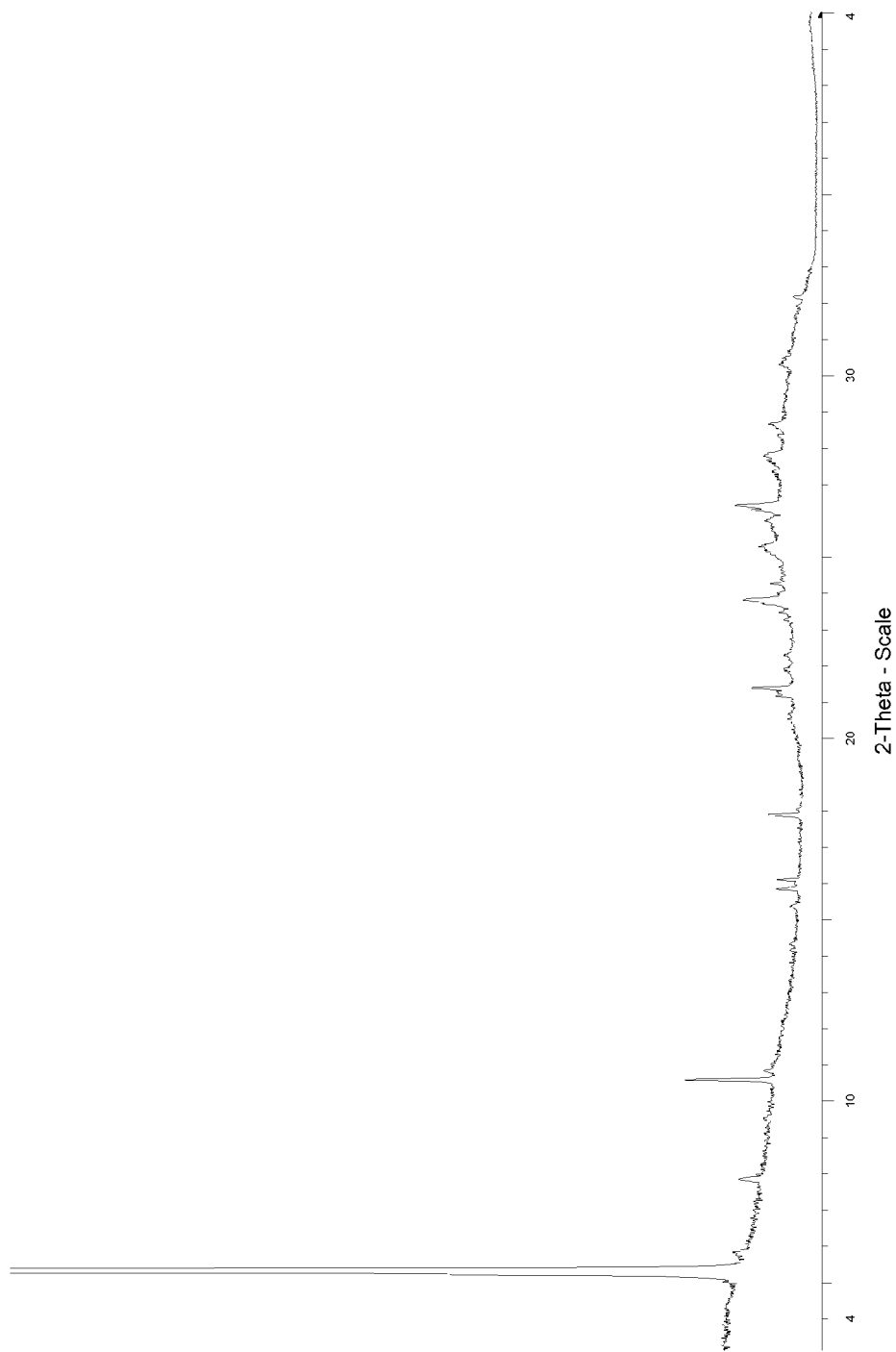
Figure 12: XRPD diagram of Form F - Diffractometer Panalytical ($\lambda_{Cu}\ K\alpha_1 = 1.5406$ Å)

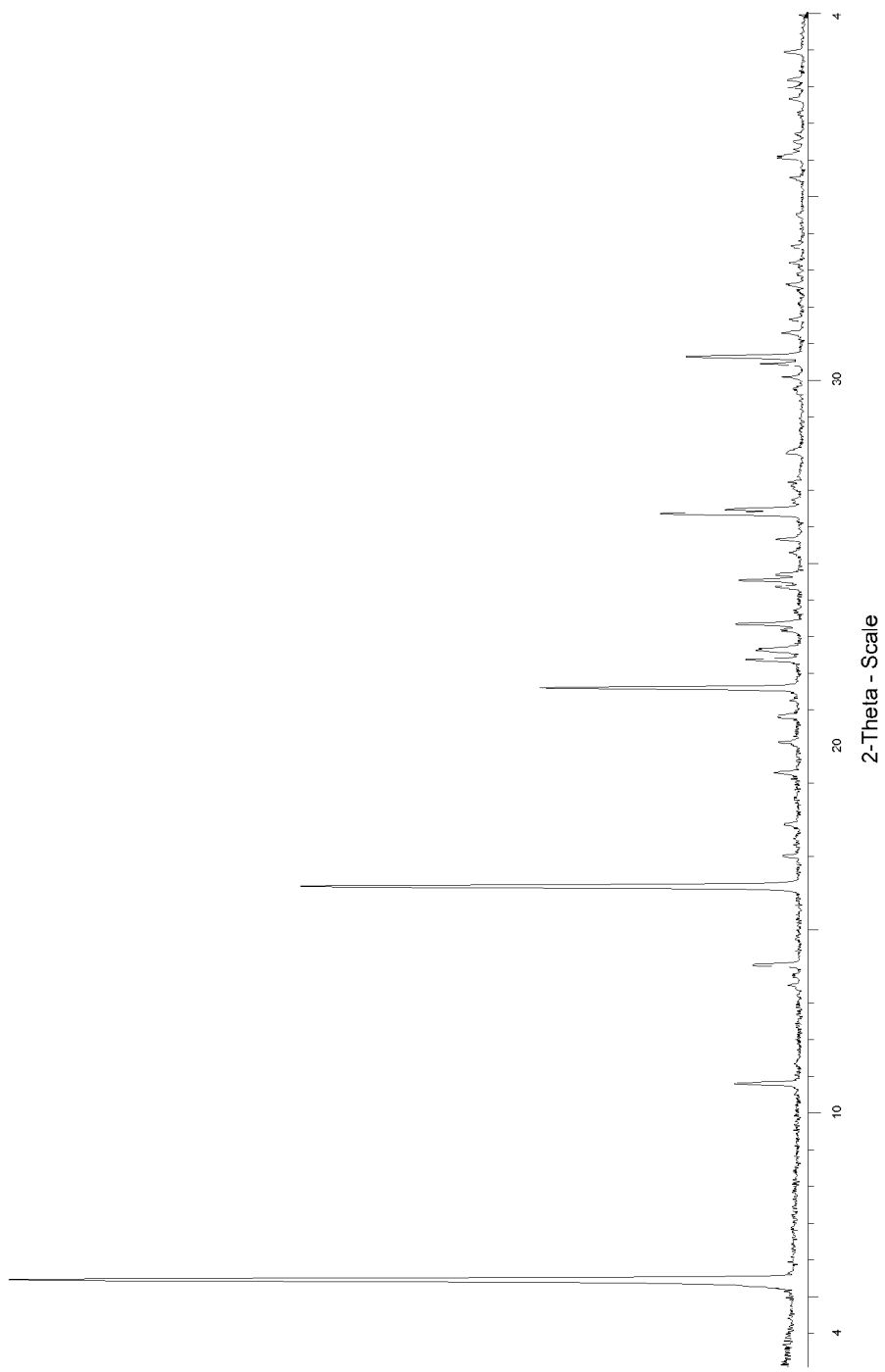
Figure 13: XRPD diagram of Form G - Diffractometer Panalytical ($\lambda_{Cu}\ K\alpha_1 = 1.5406$ Å)

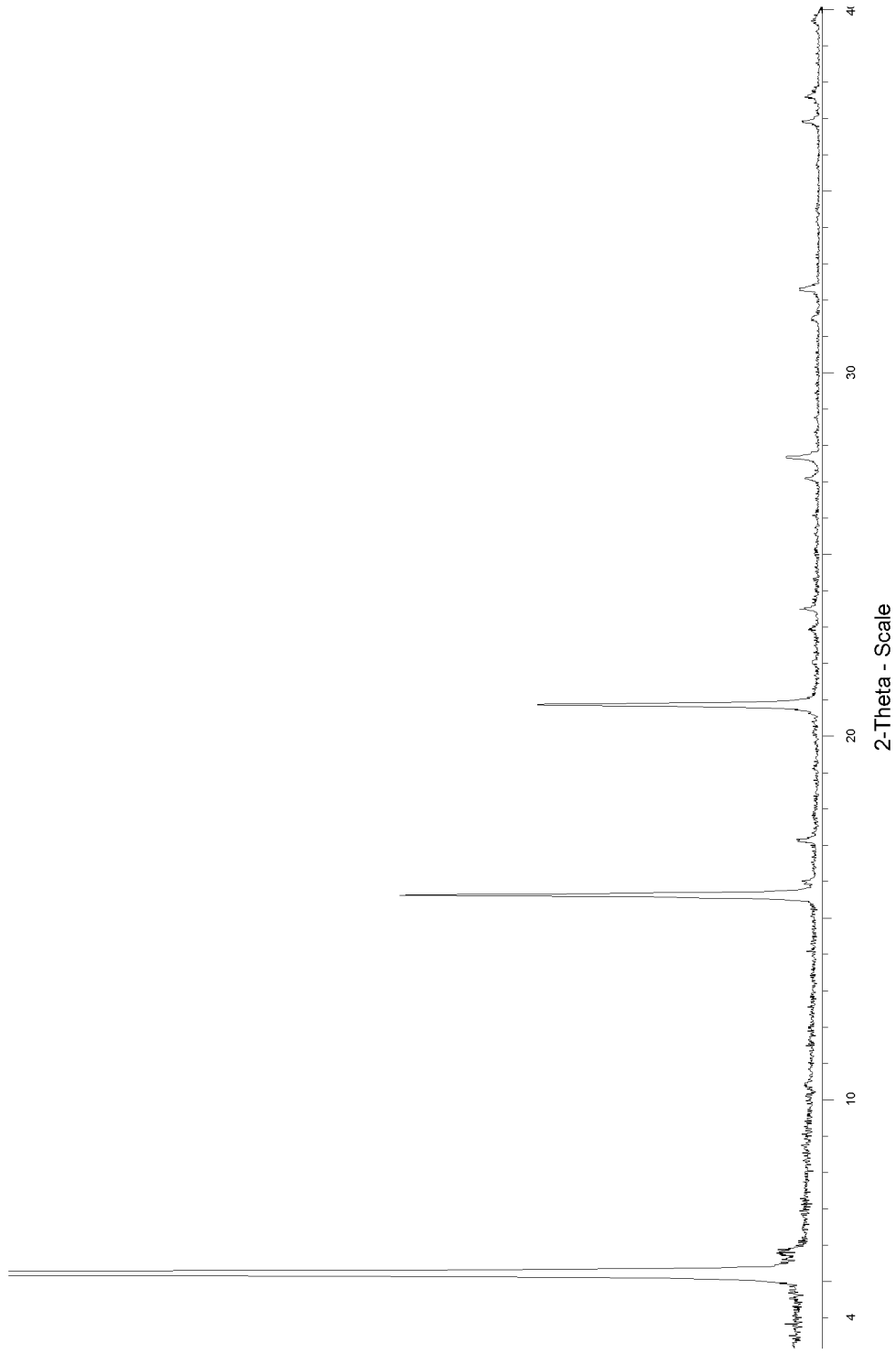
Figure 14: XRPD diagram of Form H - Diffractometer Panalytical ($\lambda_{Cu}\ K\alpha_1 = 1.5406$ Å)

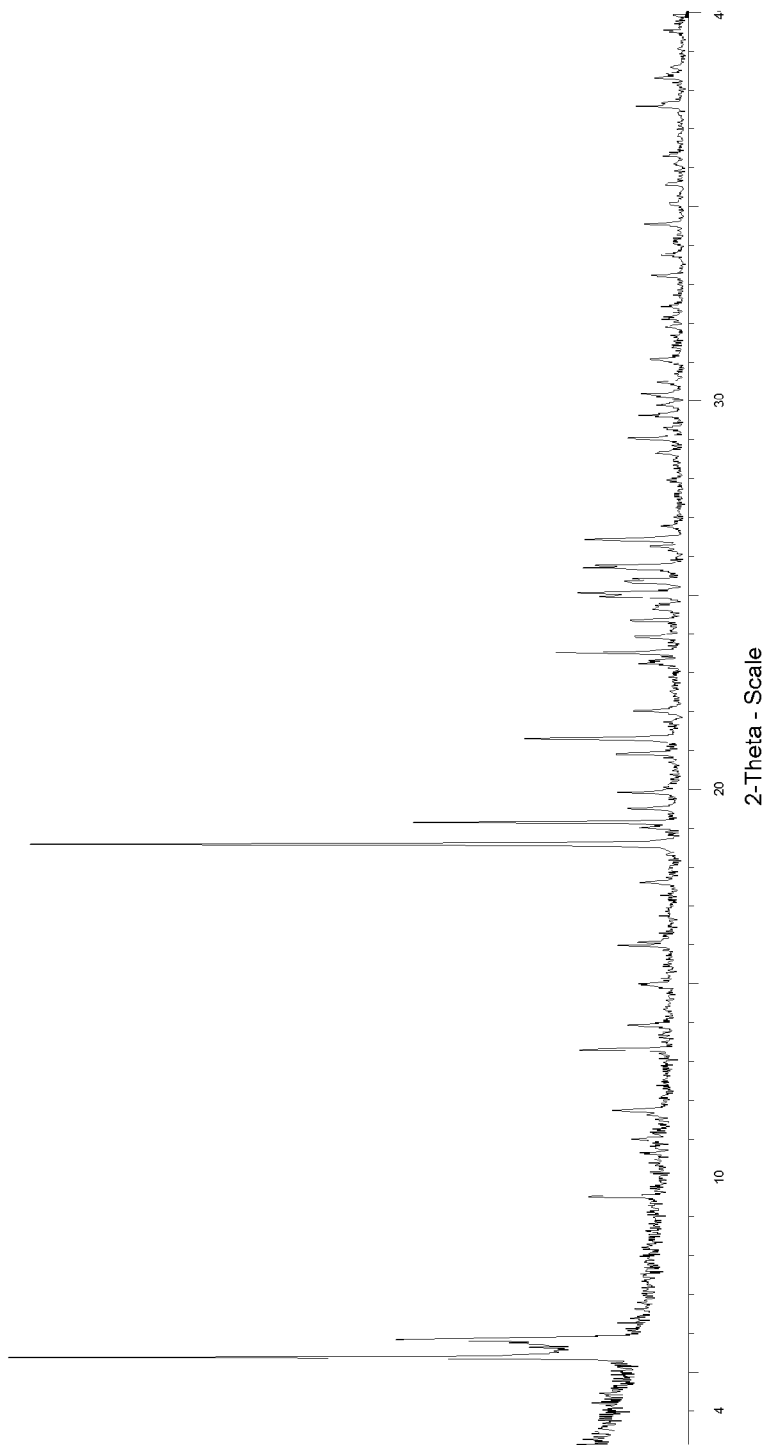
Figure 15: XRPD diagram of Form I - Diffractometer Panalytical ($\lambda_{Cu}\ K\alpha_1 = 1.5406\ \text{Å}$)

METHOD OF PREPARATION OF CRYSTAL FORMS OF 4-(CYCLOPROPYLMETHOXY)-N-(3,5-DICHLORO-1-OXIDOPYRIDYN-4-YL)-5-METHOXYPYRIDINE-2-CARBOXAMIDE AND CRYSTAL FORMS THEREOF

CROSS-REFERENCE TO RELATED APPLICATIONS

This application is a National Phase application under 35 U.S.C. §371 of International Application No. PCT/EP2013/074972 filed Nov. 28, 2013, and claims the benefit of priority of European Application No. 12306479.2 filed Nov. 28, 2012, the disclosures of each of which are incorporated herein by reference in their entirety.

TECHNICAL DOMAIN

The present invention relates to a process for preparation of novel crystal forms of 4-(cyclopropylmethoxy)-N-(3,5-dichloro-1-oxidopyridin-4-yl)-5-methoxypyridine-2-carboxamide, hereinafter referred to as Crystal Forms A to I.

The invention also relates to said Crystal Forms A to I, pharmaceutical compositions and medicament comprising them, and their therapeutic use more particularly in the prevention and/or treatment of neurodegenerative disorders, such as but not limited to Alzheimer disease or Parkinson disease.

The compound 4-(cyclopropylmethoxy)-N-(3,5-dichloro-1-oxidopyridin-4-yl)-5-methoxypyridine-2-carboxamide has the following structure of formula (I):

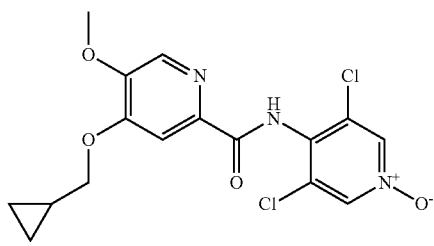

PRIOR ART

Said compound is disclosed in patent application WO95/04045 with its synthetic process.

However, none of the prior art documents describes crystallization step of this compound. WO95/04045 just describes a process which comprises a step of purification through reverse phase high pressure liquid chromatography and the compound is obtained as hemihydrate.

BRIEF DESCRIPTION OF THE INVENTION

Hence, the present invention is concerned with a process to obtain new crystal forms of compound 4-(cyclopropylmethoxy)-N-(3,5-dichloro-1-oxidopyridin-4-yl)-5-methoxypyridine-2-carboxamide of formula (I).

Indeed, the identification of new crystal forms of active ingredient useful for preventing and/or treating neurodegenerative disorders may be particularly interesting.

Further, the ability of a substance to exist in more than one crystal form is defined as crystal polymorphism and its different crystal forms are called polymorphs.

In general, crystal polymorphism is due to the ability of a compound to change its molecular conformation or to form different inter- and/or intra-molecular interactions, particularly hydrogen bonds, which is reflected in different atom arrangements in the crystal lattice of different polymorphs. Thus, polymorphs of a compound can differ notably from each other by different energies in their crystal lattices and, therefore, generally have specific physical properties in the solid state such as crystal morphology, density, melting point, colour, chemical and physical stability, hygroscopy, solubility, dissolution rate, granular properties . . . .

In other words, polymorphic forms of the same compound can exhibit different behaviours in terms of formulation, therapeutic activity and chemical and physical stability.

Unexpectedly, the inventors have discovered that the compound of formula (I) can exist in crystal forms, which are hereinafter referred to as crystal Forms A to I. Crystal Forms A, B, D and E are anhydrous forms. Crystal Form F is a hydrated form and Crystal Forms C, G and H are solvated forms. Crystal Form I is a n-propanol/water heterosolvate. Some of those Crystal Forms are particularly advantageous for the processes of formulation, for the stability of said compound and thus for the conditions of storage.

An aspect of the invention is a process for the preparation of said Crystal Forms A to I of the compound of formula (I) comprising the crystallization of 4-(cyclopropylmethoxy)-N-(3,5-dichloro-1-oxidopyridin-4-yl)-5-methoxypyridine-2-carboxamide in a pure organic solvent, a mixture of organic solvents or a mixture of organic solvent and water.

Unexpectedly, the inventors have discovered that said process is particularly advantageous over those disclosed in the prior art since it does not comprise any purification steps by chromatography and since it provides said Crystal Forms A to I of compound of 4-(cyclopropylmethoxy)-N-(3,5-dichloro-1-oxidopyridin-4-yl)-5-methoxypyridine-2-carboxamide in good yields and with good chemical purity.

Another aspect of the invention is Crystal Forms A to I of 4-(cyclopropylmethoxy)-N-(3,5-dichloro-1-oxidopyridin-4-yl)-5-methoxypyridine-2-carboxamide of formula (I) below.

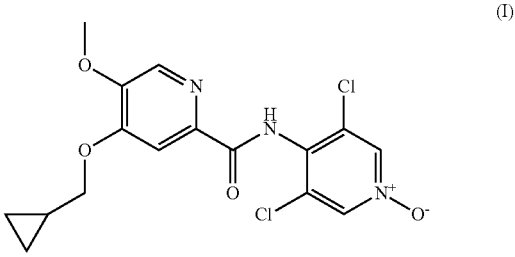 [SMILES: COc1cnc(C(=O)Nc2c(Cl)c[n+]([O-])cc2Cl)cc1OCC1CC1]

These said Crystal Forms A to I are characterized by their respective X-ray (λCo or λCu) powder diffraction pattern according to Table 1 below. For Form C, the wavelength is $\lambda_{Co}$ $K\alpha_1\alpha_2 = 1.79030$ Å and for the other Forms, the wavelength is $\lambda_{Co}$ $K\alpha_1 = 1.5406$ Å.

TABLE 1

| | Form A 1.5406 Å | Form B 1.5406 Å | Form C 1.79030 Å | Form D 1.5406 Å | Form E 1.5406 Å | Form F 1.5406 Å | Form G 1.5406 Å | Form H 1.5406 Å | Form I 1.5406 Å |
|---|---|---|---|---|---|---|---|---|---|
| 1 | 9.5 | 9.6 | 6.2 | 5.8 | 3.2 | 5.3 | 5.4 | 5.2 | 5.3 |
| 2 | 10.9 | 10.6 | 8.9 | 9.3 | 5.8 | 7.8 | 10.7 | 15.6 | 5.8 |
| 3 | 11.7 | 11.5 | 16.4 | 11.6 | 6.3 | 10.5 | 13.9 | 17.1 | 9.5 |
| 4 | 13.3 | 11.9 | 17.6 | 12.7 | 11.9 | 10.8 | 16.2 | 20.9 | 11.7 |
| 5 | 13.9 | 12.9 | 18.5 | 13.7 | 12.2 | 15.8 | 17.1 | 23.5 | 13.3 |
| 6 | 14.9 | 14.1 | 20.5 | 15.5 | 12.3 | 16.1 | 17.9 | 27.1 | 13.9 |
| 7 | 16.1 | 17.3 | 24.8 | 16.2 | 12.6 | 17.9 | 19.3 | 27.7 | 14.9 |
| 8 | 17.6 | 17.5 | 27.6 | 16.9 | 13.7 | 21.4 | 20.1 | 31.5 | 17.6 |
| 9 | 18.6 | 18.3 | 30.7 | 17.7 | 14.6 | 23.8 | 20.8 | 32.3 | 18.6 |
| 10 | 19.2 | 18.5 | 33.1 | 18.6 | 15.8 | 24.3 | 21.6 | 36.9 | 19.1 |

In a further aspect of the invention, these said Crystal Forms A to I are characterized by their respective X-ray (λCo or λCu) powder diffraction pattern according to Table 2 below. For Form C, the wavelength is $\lambda_{Co} K\alpha_1\alpha_2 = 1.79030$ Å and for the other Forms, the wavelength is $\lambda_{Cu} K\alpha_1 = 1.5406$ Å.

TABLE 2

| | Form A 1.5406 Å | Form B 1.5406 Å | Form C 1.79030 Å | Form D 1.5406 Å | Form E 1.5406 Å | Form F 1.5406 Å | Form G 1.5406 Å | Form H 1.5406 Å | Form I 1.5406 Å |
|---|---|---|---|---|---|---|---|---|---|
| 1 | 10.9 | 10.6 | 8.9 | 5.8 | 3.2 | 7.8 | 20.1 | 23.5 | 5.3 |
| 2 | 13.3 | 17.3 | 20.5 | 12.7 | 12.2 | 21.4 | 21.6 | 27.1 | |
| 3 | 14.9 | 18.3 | 24.8 | 15.5 | 12.3 | 23.8 | | 31.5 | |
| 4 | 19.2 | | 30.7 | 16.9 | 14.6 | 24.3 | | 32.3 | |
| 5 | | | 33.1 | | 15.8 | | | 36.9 | |

In another aspect of the invention is a medicament, comprising a crystal form of compound of formula (I) among Crystal Forms A to I.

The said Crystal Forms A to I can advantageously be used directly as Active Pharmaceutical Ingredients (API) to prepare formulations.

In a further aspect of the invention is a pharmaceutical composition comprising a crystal form of compound of formula (I) and also at least one pharmaceutically acceptable excipient.

In a further aspect of the invention is the use of a crystal form of compound of formula (I) in the prevention and/or treatment of neurodegenerative disorders.

BRIEF DESCRIPTION OF THE DRAWINGS

FIG. 12 is an X-ray Powder Diffractogram (λCu) of Crystal Form F of 4-(cyclopropylmethoxy)-N-(3,5-dichloro-1-oxidopyridin-4-yl)-5-methoxypyridine-2-carboxamide of the present invention.

FIG. 13 is an X-ray Powder Diffractogram (λCu) of Crystal Form G of 4-(cyclopropylmethoxy)-N-(3,5-dichloro-1-oxidopyridin-4-yl)-5-methoxypyridine-2-carboxamide of the present invention.

FIG. 14 is an X-ray Powder Diffractogram (λCu) of Crystal Form H of 4-(cyclopropylmethoxy)-N-(3,5-dichloro-1-oxidopyridin-4-yl)-5-methoxypyridine-2-carboxamide of the present invention FIG. 15 is an X-ray Powder Diffractogram (λCu) of Crystal Form I of 4-(cyclopropylmethoxy)-N-(3,5-dichloro-1-oxidopyridin-4-yl)-5-methoxypyridine-2-carboxamide of the present invention

DESCRIPTION OF THE INVENTION

Process

Figure 1:
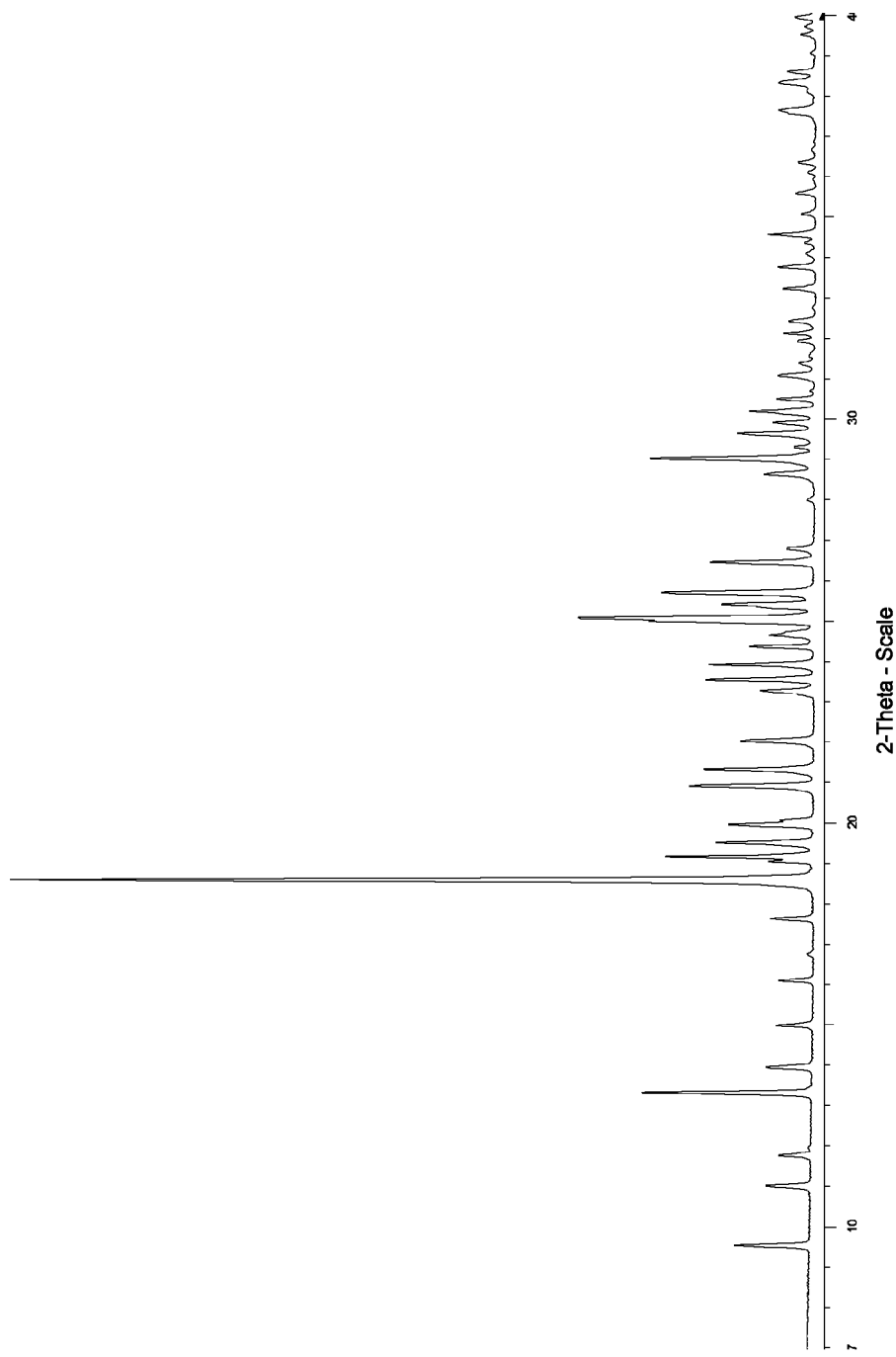
FIG. 1 is an X-ray Powder Diffractogram (λCu) of Crystal Form A of 4-(cyclopropylmethoxy)-N-(3,5-dichloro-1-oxidopyridin-4-yl)-5-methoxypyridine-2-carboxamide of the present invention.

An aspect of the present invention is a process for the preparation of said Crystal Forms A to I of 4-(cyclopropylmethoxy)-N-(3,5-dichloro-1-oxidopyridin-4-yl)-5-methoxypyridine-2-carboxamide.

Thus, the present invention is directed to a particular process for preparing Crystal Forms A to I of 4-(cyclopropylmethoxy)-N-(3,5-dichloro-1-oxidopyridin-4-yl)-5-methoxypyridine-2-carboxamide comprising at least heating of 4-(cyclopropylmethoxy)-N-(3,5-dichloro-1-oxidopyridin-4-yl)-5-methoxypyridine-2-carboxamide in a pure organic solvent, a mixture of organic solvents or a mixture of organic solvent and water until dissolution; cooling to induce crystallization; recovering the resulting crystal by filtration, and drying the crystals of Form A to I.

The organic solvent used in dissolving 4-(cyclopropylmethoxy)-N-(3,5-dichloro-1-oxidopyridin-4-yl)-5-methoxypyridine-2-carboxamide may be an alcohol such as methanol, propanol, ethanol or isopropanol, an ester such as ethyl acetate, an aromatic solvent such as toluene, a polar solvent such as acetonitrile, a cetone such as acetone, a sulphur solvent such as dimethylsulfoxide, a mixture of ethanol and water, methanol and water, tetrahydrofuran and water or acetonitrile and water.

Further, said process is particularly advantageous over those disclosed in the prior art since it does not comprise any purification steps by chromatography and since it provides said Crystal Forms A to I of compound of 4-(cyclopropylmethoxy)-N-(3,5-dichloro-1-oxidopyridin-4-yl)-5-methoxypyridine-2-carboxamide in good yields and with good chemical purity.

By "good yield" in the present invention, it is meant that said Crystal Forms A to I is obtained in a yield higher than or equal to 77%.

As used herein a "good chemical purity" is a purity which is higher than or equal to 99.5%.

Crystals Forms A to I According to the Invention

The present invention provides novel crystal forms of 4-(cyclopropylmethoxy)-N-(3,5-dichloro-1-oxidopyridin-4-yl)-5-methoxypyridine-2-carboxamide of formula (I)

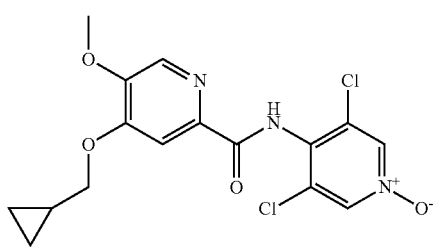

(I)

which are designated as Crystal Forms A to I.

Crystals Forms A, B, D and E of 4-(cyclopropylmethoxy)-N-(3,5-dichloro-1-oxidopyridin-4-yl)-5-methoxypyridine-2-carboxamide are anhydrous compounds.

Crystal Form F of 4-(cyclopropylmethoxy)-N-(3,5-dichloro-1-oxidopyridin-4-yl)-5-methoxypyridine-2-carboxamide is a hydrated form, more particularly Crystal Form F is a dihydrated form.

Crystal Forms C, G and H of 4-(cyclopropylmethoxy)-N-(3,5-dichloro-1-oxidopyridin-4-yl)-5-methoxypyridine-2-carboxamide are solvated forms. For example, Crystal Form G is a DMSO solvate and Crystal Form H is an acetone solvate. Crystal Form I is a n-propanol/water hetero-solvate More particularly, said Crystal Forms A to I of 4-(cyclopropylmethoxy)-N-(3,5-dichloro-1-oxidopyridin-4-yl)-5-methoxypyridine-2-carboxamide have an X-ray (λCo or λCu) powder diffraction pattern similar as described in Table 1 above and FIGS. 1, 4 to 6, 9 and 12 to 15.

In another embodiment, said Crystal Forms A, D and E of 4-(cyclopropylmethoxy)-N-(3,5-dichloro-1-oxidopyridin-4-yl)-5-methoxypyridine-2-carboxamide have been identified and physically characterised by thermo-gravimetric analysis (TGA).

In another embodiment, said Crystal Forms A to H of 4-(cyclopropylmethoxy)-N-(3,5-dichloro-1-oxidopyridin-4-yl)-5-methoxypyridine-2-carboxamide have been identified and physically caracterized by water sorption/desorption 25° C. isotherm.

In an aspect, the invention provides Crystal Forms A to I of 4-(cyclopropylmethoxy)-N-(3,5-dichloro-1-oxidopyridin-4-yl)-5-methoxypyridine-2-carboxamide as defined herein substantially free of any other polymorph(s).

In a further aspect, Crystal Forms A to I of 4-(cyclopropylmethoxy)-N-(3,5-dichloro-1-oxidopyridin-4-yl)-5-methoxypyridine-2-carboxamide as herein defined are substantially free of impurities.

By "substantially free", it is meant that Crystal Forms A to I comprise less than 10%, preferably less than 2% of any other polymorph(s) or impurity or impurities.

Form A

Figure 2:
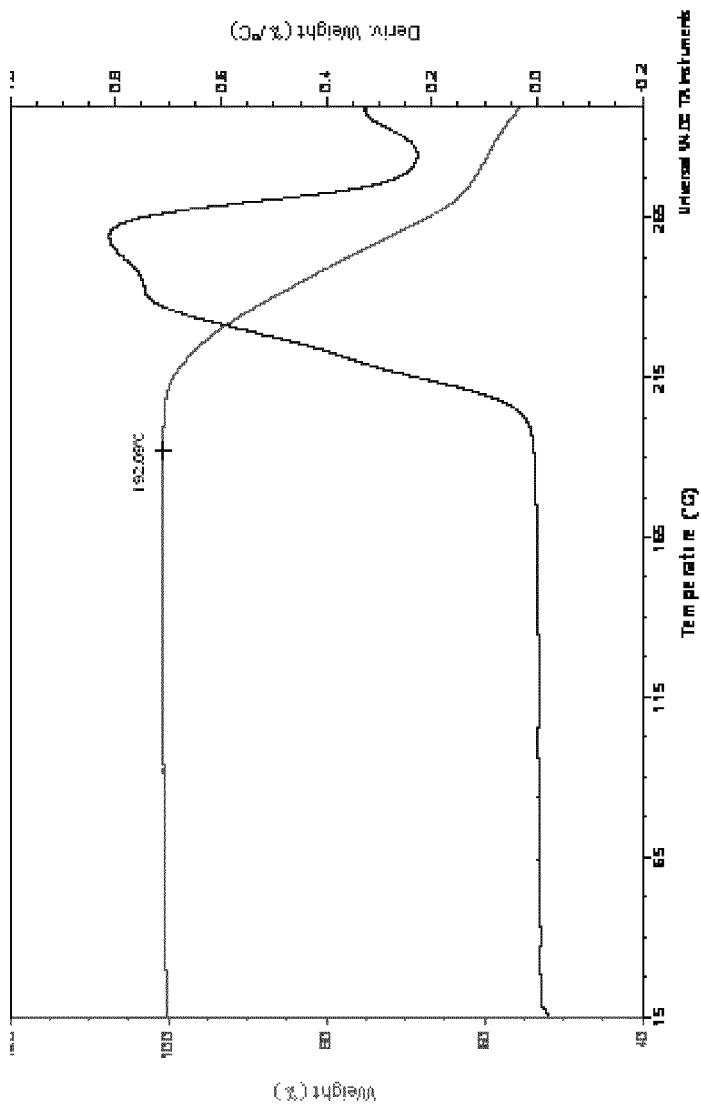
FIG. 2 is Thermo-Gravimetric Analysis data of Crystal Form A of 4-(cyclopropylmethoxy)-N-(3,5-dichloro-1-oxidopyridin-4-yl)-5-methoxypyridine-2-carboxamide of the present invention.

Crystal Form A has a thermo-gravimetric analysis data substantially identical to the one of FIG. 2 in which no weight loss is observed from room temperature up to 190° C., temperature beyond which thermal decomposition is observed.

Figure 3:
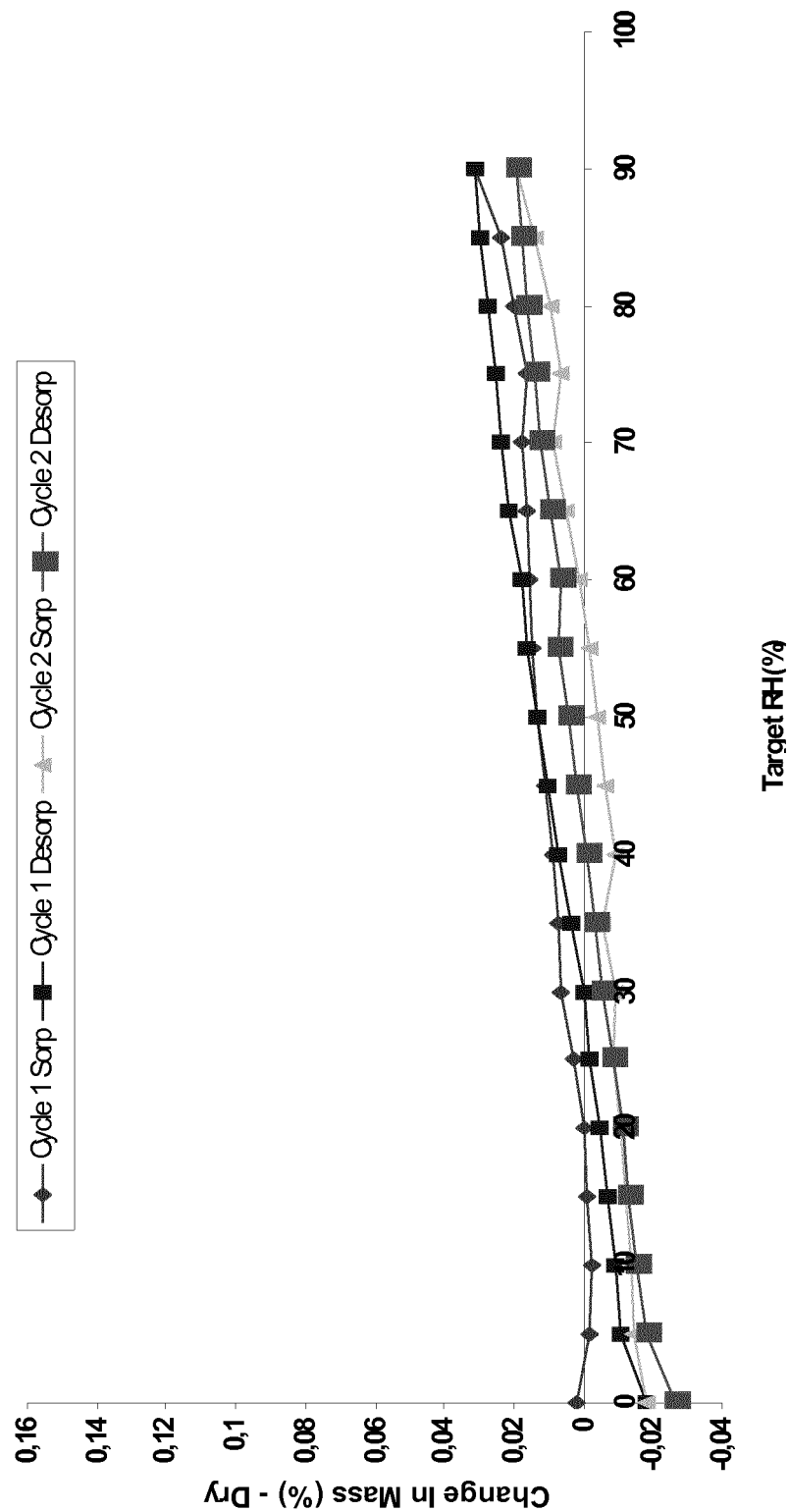
FIG. 3 shows water sorption/desorption isotherms recorded at 25° C. of Crystal Form A of 4-(cyclopropylmethoxy)-N-(3,5-dichloro-1-oxidopyridin-4-yl)-5-methoxypyridine-2-carboxamide of the present invention.
Figure 4:
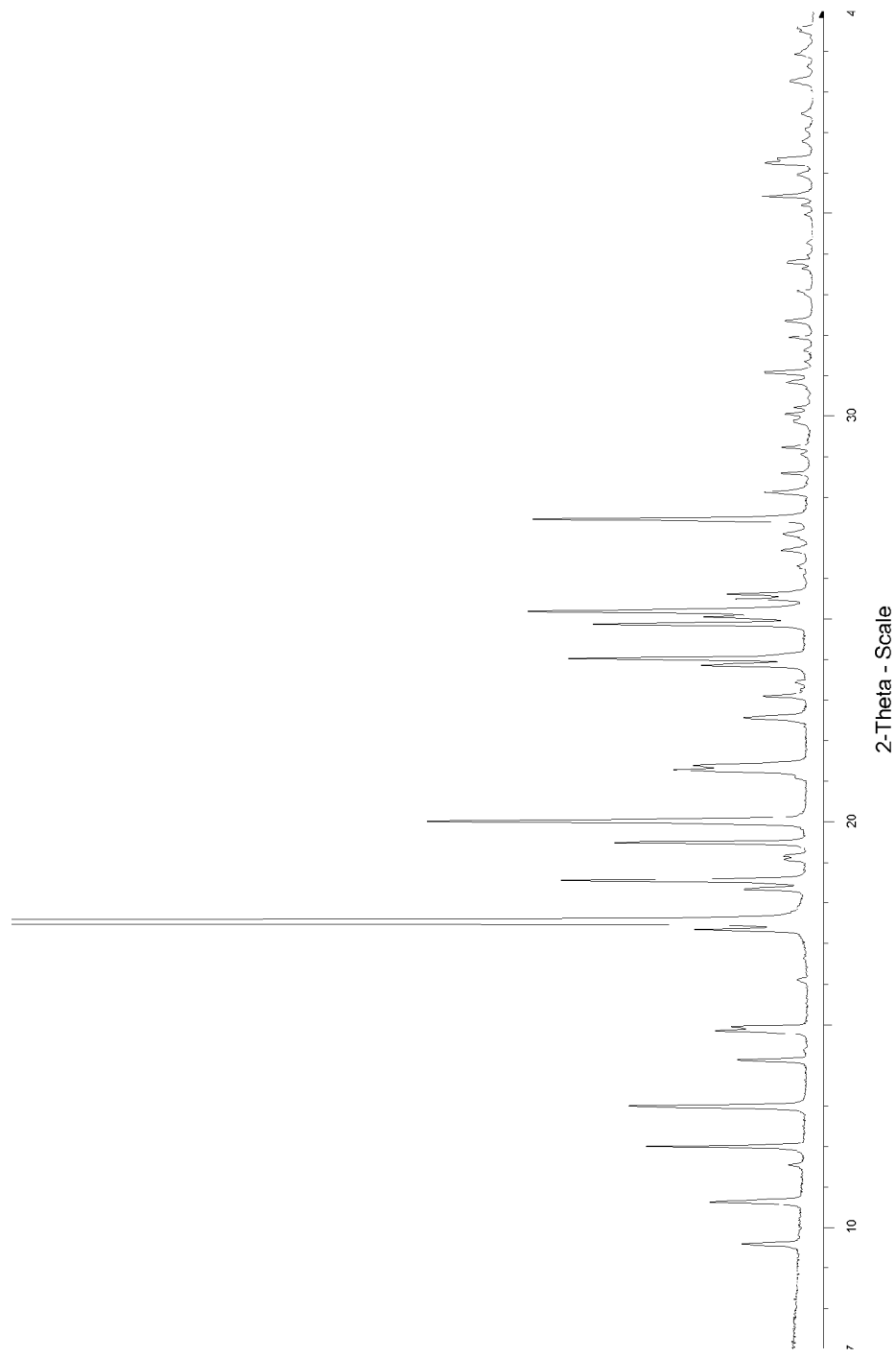
FIG. 4 is an X-ray Powder Diffractogram (λCu) of Crystal Form B of 4-(cyclopropylmethoxy)-N-(3,5-dichloro-1-oxidopyridin-4-yl)-5-methoxypyridine-2-carboxamide of the present invention, recorded at 120° C.

Crystal Form A of 4-(cyclopropylmethoxy)-N-(3,5-dichloro-1-oxidopyridin-4-yl)-5-methoxypyridine-2-carboxamide has a water sorption/desorption 25° C. isotherm substantially identical to that of FIG. 3 in which no significant water uptake is observed up to 90% of relative humidity (RH). Said Crystal Form A is thus not hygroscopic.

The said crystal Form A is a stable anhydrous and non-hygroscopic crystal solid form. These characteristics are particularly advantageous for the processes of formulation, for the stability of said compound and thus for the conditions of storage.

Crystal Form A is of particular interest because of its behaviour under mechanical strain. The effect of 30 seconds of mortar grinding was evaluated. XRPD experiment shows that this kind of mechanical treatment caused no observed polymorphic transition, but the appearance of amorphous phase was detected. The behaviour of amorphous phase present in ground form A was also studied. No recrystallization of the amorphous phase was detected through sorption/desorption of water at 25° C. Nevertheless, maturation of ground samples in pure water for 6 days at room temperature led to partial recrystallization of the amorphous phase into form A.

Therefore Crystal Form A of 4-(cyclopropylmethoxy)-N-(3,5-dichloro-1-oxidopyridin-4-yl)-5-methoxypyridine-2-carboxamide is advantageous.

Crystal Form A is also of particular interest because it has been demonstrated that jet-milling is feasible without any impact on the crystalline form. A particle size close to 5 μm could be reached. The DSC analyses indicate that there is no modification of the crystalline structure before and after jet-milling of Form A.

Form B

Crystal Form B is obtained:
from Crystal Form A, above 100° C. and remains stable from 100 to 190° C., temperature beyond which thermal decomposition is observed, and,
from Crystals Forms D and E above 180° C.

When Form B is cooled back at room temperature, Form A is obtained.

Crystal Form B is of particular interest because the solid-solid transition A←→B is completely reversible upon cooling. Form B allows to access to Form A from Form D.

Form C

Crystal Form C was transformed into Crystal Form D and amorphous phase after 15 months of storage in ambient conditions.

Form D

Figure 7:
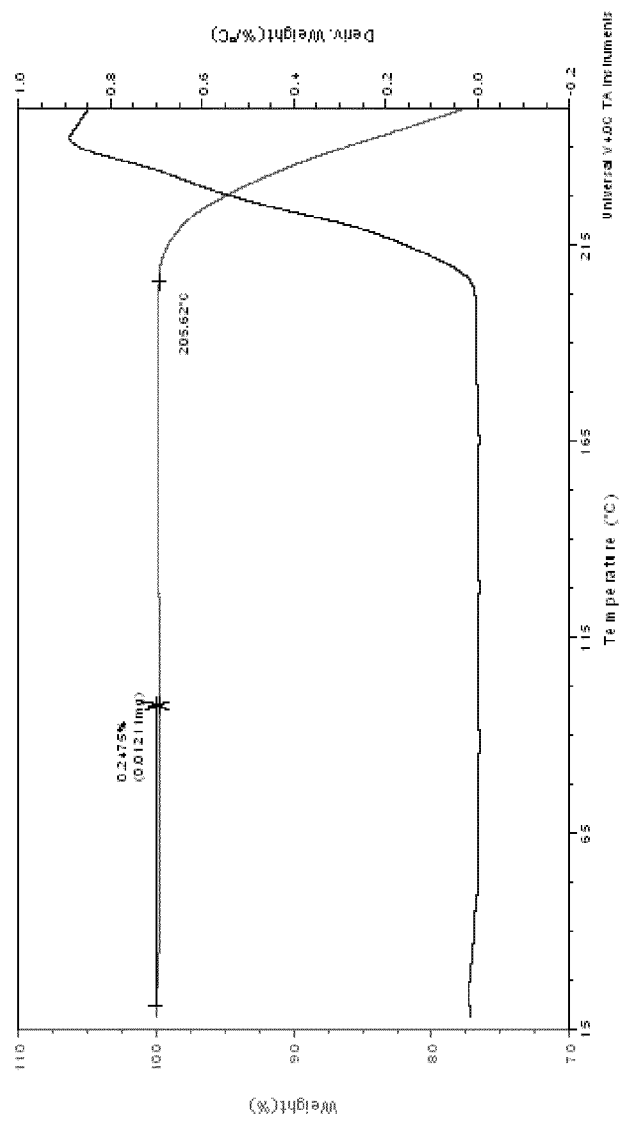
FIG. 7 is Thermo-Gravimetric Analysis data of Crystal Form D of 4-(cyclopropylmethoxy)-N-(3,5-dichloro-1-oxidopyridin-4-yl)-5-methoxypyridine-2-carboxamide of the present invention.

Crystal Form D has a thermo-gravimetric analysis data substantially identical to the one of FIG. 7 in which is recorded a slight weight loss of 0.2% between 20 and 100° C. and no weight loss is between 100 and 205° C., temperature beyond which thermal decomposition is observed.

Figure 8:
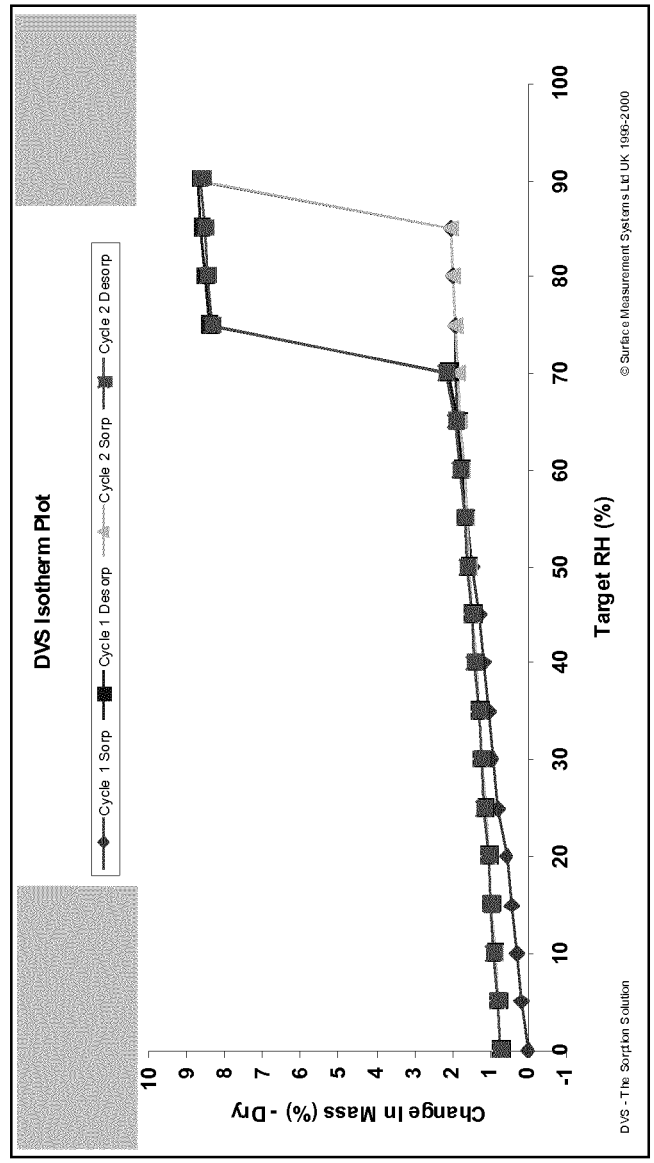
FIG. 8 shows water sorption/desorption isotherms recorded at 25° C. of Crystal Form D of 4-(cyclopropylmethoxy)-N-(3,5-dichloro-1-oxidopyridin-4-yl)-5-methoxypyridine-2-carboxamide of the present invention.
Figure 9:
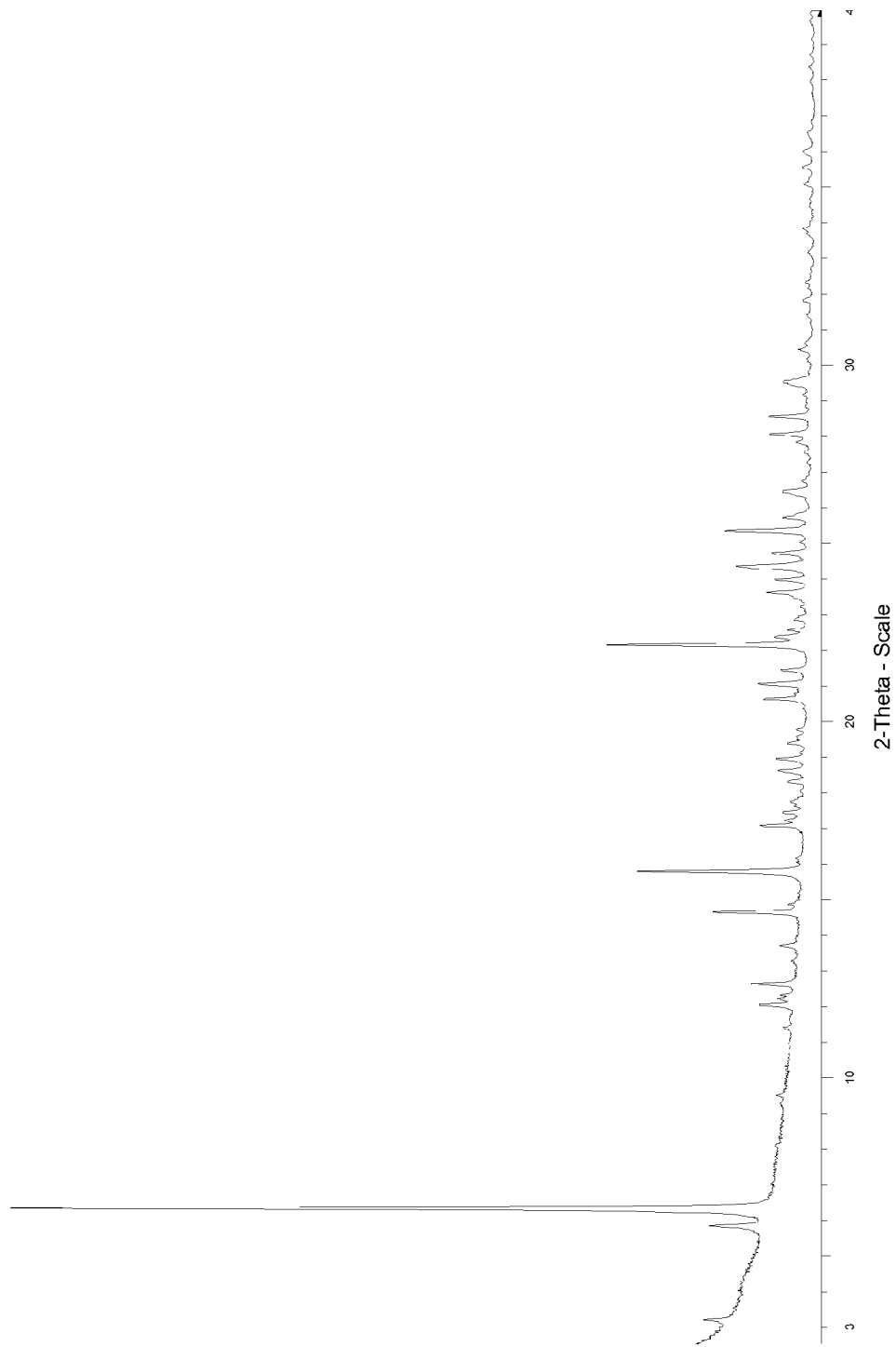
FIG. 9 is an X-ray Powder Diffractogram (λCu) of Crystal Form E of 4-(cyclopropylmethoxy)-N-(3,5-dichloro-1-oxidopyridin-4-yl)-5-methoxypyridine-2-carboxamide of the present invention.

Crystal Form D of 4-(cyclopropylmethoxy)-N-(3,5-dichloro-1-oxidopyridin-4-yl)-5-methoxypyridine-2-carboxamide has a water sorption/desorption 25° C. isotherm substantially identical to that of FIG. 8 which shows two superimposable cycles with significant hysteresis between 70 to 90% of relative humidity (RH).

The water sorption process of Crystal Form D can be divided into two steps. The first step is observed between 0% and 85% RH and corresponds to a continuous water uptake. The second step is observed between 85% and 90% RH and corresponds to an appreciable water uptake of 6.9%. Therefore, the total water gain at 90% RH is 8.7%, which corresponds to 2 moles of water.

The water desorption process of Crystal Form D can be divided into three distinct steps. The first step is observed between 90% and 75% RH and corresponds to an appreciable hysteresis. The second step is observed between 75% and 70% RH and corresponds to a water desorption of 6.4%. The last step is observed between 70% and 0% RH and corresponds to a slow, continuous loss of 1.3% of water without hysteresis takes place.

Crystal Form D is physically unaltered up to 110° C. and from 0 to 85% RH. Upon heating, Form D can be transformed into Form B through a concomitant recrystallization process: 1-directly, and 2-through a prior irreversible solid-solid transition into Form E, followed by melting and recrystallization of Form E into Form B. At 180° C., pure Form B is obtained. When the sample, totally transformed into Form B is cooled back to room conditions, Form A, is obtained.

Crystal Form D is of particular interest because it has been demonstrated that jet-milling is feasible without any impact on the crystalline form. A particle size close to 5 µm could be reached. Moreover, although the DSC analyses could indicate a trend to amorphisation, XRPD analysis shows no modification of the crystalline structure after jet-milling.

Therefore Crystal Form D of 4-(cyclopropylmethoxy)-N-(3,5-dichloro-1-oxidopyridin-4-yl)-5-methoxypyridine-2-carboxamide is advantageous.

Form E

Figure 10:
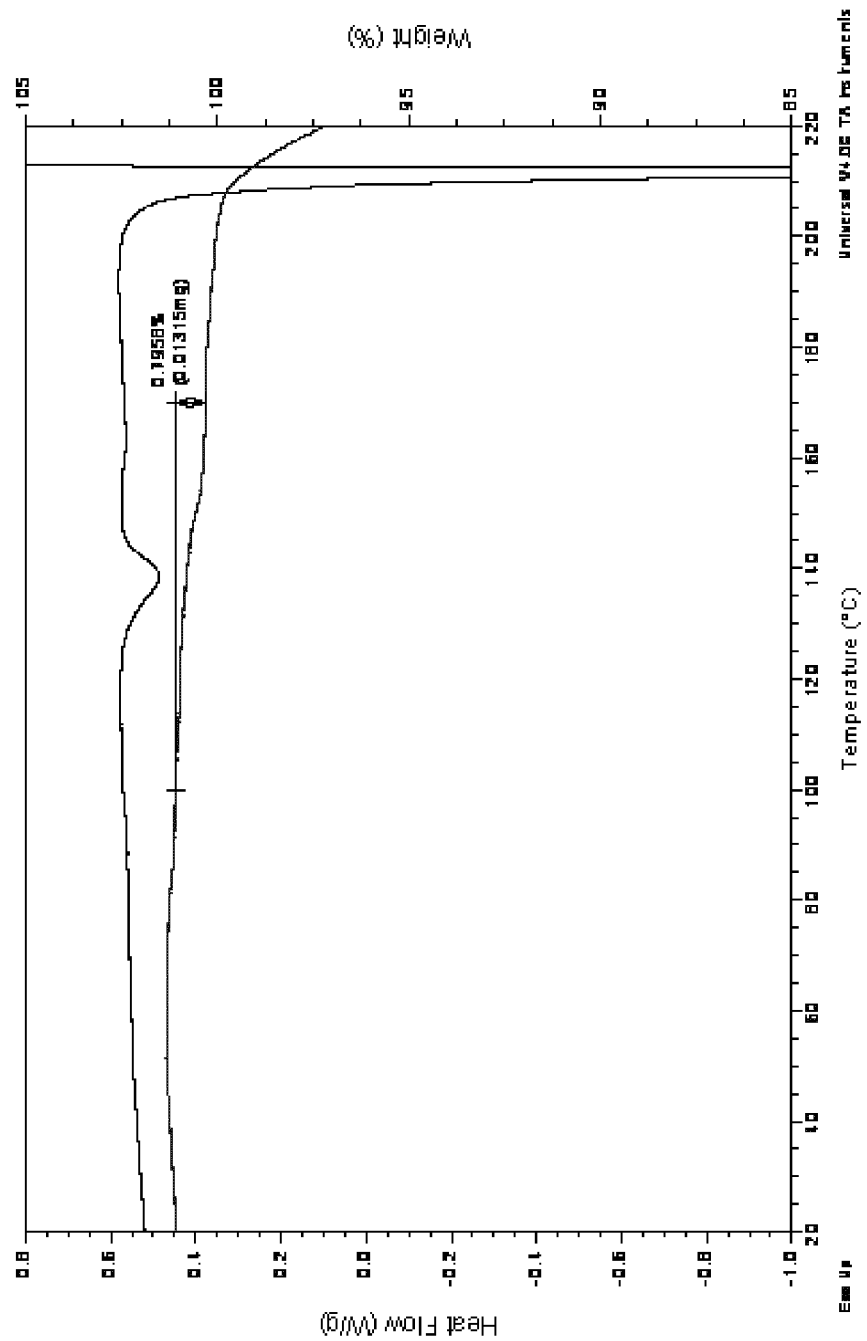
FIG. 10 is Thermo-Gravimetric Analysis data of Crystal Form E of 4-(cyclopropylmethoxy)-N-(3,5-dichloro-1-oxidopyridin-4-yl)-5-methoxypyridine-2-carboxamide of the present invention.

Crystal Form E has a thermo-gravimetric analysis data substantially identical to the one of FIG. 10 in which is recorded no weight loss from room temperature to 100° C. and a slight weight loss of 0.8% between 100 and 170° C., temperatures corresponding of some crystallization solvent.

Crystal Form E is obtained from Crystal Form D in two stages through a prior irreversible solid-solid transition at 110° C. At 140° C., this Crystal Form E can be transformed into Crystal Form B by a concomitant melting/recrystallization process.

Crystal Form E is also obtained by crystallization in THF via fast evaporation at 60° C.

Crystal Form E is of particular interest because it is stable under room conditions and it may be obtain via crystallisation.

Form F

Crystal Form F is obtained from Crystal Form D above 70% RH.

Crystal Form F is of particular interest because it has a restricted domain of stability from 75% to 90% RH, at 25° C. It may have advantage in wet or aqueous environment.

Form G

Crystal Form G is obtained only in DMSO:
through dissolution in DMSO under heating followed by crystallization through cooling, or
after slow evaporation of the DMSO solvent.

After a slight heating, Crystal Form G desolvates easily at 70° C. into Crystal Form D.

Crystal Form G is of particular interest because it is a DMSO solvate.

Form H

Crystal Form H desolvates easily into Crystal Form D, after a slight heating.

Crystal Form H is of particular interest because it is an acetone solvate.

Form I

Crystal Form I was obtained once through dissolution in n-propanol/water (90/10) under heating, followed by crystallization through cooling.

Crystal Form I is a n-propanol/water hetero-solvate. Upon heating, form I desolvates easily into form D.

Crystal Form I is of particular interest because it is a n-propanol/water hetero-solvate giving access to Form D.

As explained above, the skilled man in the art understand that due to the different transition pathway between these crystal forms, some of these crystal forms are of particular interest because they can be used as starting material to obtain other crystal forms. Especially, Crystal Forms C, F, G, H and I allow to access to Form D. And Form D allows to access to Form A.

The instrumentation and method are described in the Experimental part below.

Application

The present invention is also directed to a medicament comprising said Form A of 4-(cyclopropylmethoxy)-N-(3, 5-dichloro-1-oxidopyridin-4-yl)-5-methoxypyridine-2-carboxamide.

The said crystal Form A can advantageously be used directly as an Active Pharmaceutical Ingredient (API) to prepare formulations.

Thus, the present invention also relates to a pharmaceutical composition comprising said Form A of 4-(cyclopropylmethoxy)-N-(3,5-dichloro-1-oxidopyridin-4-yl)-5-methoxypyridine-2-carboxamide and also at least one pharmaceutically acceptable excipient.

All components of the present compositions must be pharmaceutically acceptable. As used herein, a "pharmaceutically acceptable" component is one that is suitable for use with humans and/or other animals without undue adverse side effects (such as toxicity, irritation and allergic response) commensurate with a reasonable benefit/risk ratio.

The compositions of the present invention are generally administered to patients, which include, but are not limited to, mammals, for example, humans, by conventional routes known in the art.

A further aspect of the invention is a pharmaceutical composition comprising a compound of formula (I) and also at least one pharmaceutically acceptable excipient.

In a further aspect, the present invention provides, said crystal Form A of 4-(cyclopropylmethoxy)-N-(3,5-dichloro-1-oxidopyridin-4-yl)-5-methoxypyridine-2-carboxamide for its use for preventing and/or treating neurodegenerative disorders such as but not limited to Alzheimer disease or Parkinson disease.

EXAMPLES

The crude compound 4-(cyclopropylmethoxy)-N-(3,5-dichloro-1-oxidopyridin-4-yl)-5-methoxypyridine-2-carboxamide may be synthesized according to the following process:

Step 1: Preparation of 4-cyclopropylmethoxy-5-methoxy-2-hydroxymethyl-pyridine 2-Hydroxymethyl-5-methoxypyridin-4-(1H)-one is heated with bromomethylcyclopropane in dimethylformamide (DMF), in the presence of cesium carbonate (Cs2CO3). DMF is eliminated by distillation and replaced by dichloromethane (CH2Cl2). After washing with water, CH2Cl2 is exchanged with xylene. 4-cyclopropylmethoxy-5-methoxy-2-hydroxymethyl-pyridine is isolated by filtration, washed with tert-butylmethyl ether (MTBE) and dried.

Step 2: Preparation of 4-cyclopropylmethoxy-5-methoxy-pyridine-2-carboxylic acid Potassium permanganate (KMnO4) is added to a mixture of sodium carbonate (Na2CO3) and 4-cyclopropylmethoxy-5-methoxy-2-hydroxymethyl-pyridine suspended in water. The aqueous mixture is filtered and the filtrate is washed with dichloromethane, treated with sodium thiosulfate (Na2S2O3), acidified and concentrated. 4-cyclopropylmethoxy-5-methoxypyridine-2-carboxylic acid is isolated by filtration, washed with water and dried.

Step 3: Preparation of crude 4-(cyclopropylmethoxy)-N-(3,5-dichloro-1-oxidopyridin-4-yl)-5-methoxypyridine-2-carboxamide A mixture of 4-cyclopropylmethoxy-5-methoxypyridine-2-carboxylic acid and 3,5-Dichloro-4-aminopyridin-1-oxide is heated in ethyl acetate, in the presence of npropylphosphonic anhydride, triethylamine (TEA) and 4-dimethylaminopyridine (DMAP). After hydrolytic work-up, crude 4-(cyclopropylmethoxy)-N-(3,5-dichloro-1-oxidopyridin-4-yl)-5-methoxypyridine-2-carboxamide is isolated by filtration and drying.

Example 1

Preparation of crystal Form A of 4-(cyclopropylmethoxy)-N-(3,5-dichloro-1-oxidopyridin-4-yl)-5-methoxypyridine-2-carboxamide of formula (I)

15.9 g of 4-(cyclopropylmethoxy)-N-(3,5-dichloro-1-oxidopyridin-4-yl)-5-methoxypyridine-2-carboxamide was dissolved by heating to 95° C. in 223 ml of propanol. The solution was cooled to 20° C., the precipitate filtered and dried at 40° C. under vacuum for 18 h to obtain 14.7 g of crystal Form A of 4-(cyclopropylmethoxy)-N-(3,5-dichloro-1-oxidopyridin-4-yl)-5-methoxypyridine-2-carboxamide.

Example 2

Preparation of crystal Form A of 4-(cyclopropylmethoxy)-N-(3,5-dichloro-1-oxidopyridin-4-yl)-5-methoxypyridine-2-carboxamide of formula (I)

1 g of 4-(cyclopropylmethoxy)-N-(3,5-dichloro-1-oxidopyridin-4-yl)-5-methoxypyridine-2-carboxamide was dissolved by heating to reflux in 12 ml of toluene. The solution was cooled to room temperature, the precipitate filtered and dried to obtain crystal Form A of 4-(cyclopropylmethoxy)-N-(3,5-dichloro-1-oxidopyridin-4-yl)-5-methoxypyridine-2-carboxamide.

Example 3

Preparation of crystal Form A of 4-(cyclopropylmethoxy)-N-(3,5-dichloro-1-oxidopyridin-4-yl)-5-methoxypyridine-2-carboxamide of formula (I)

1 g of 4-(cyclopropylmethoxy)-N-(3,5-dichloro-1-oxidopyridin-4-yl)-5-methoxypyridine-2-carboxamide was dissolved by heating to reflux in 34 ml of isopropanol. The solution was cooled to room temperature, the precipitate filtered and dried to obtain crystal Form A of 4-(cyclopropylmethoxy)-N-(3,5-dichloro-1-oxidopyridin-4-yl)-5-methoxypyridine-2-carboxamide.

Example 4

Preparation of crystal Form A of 4-(cyclopropylmethoxy)-N-(3,5-dichloro-1-oxidopyridin-4-yl)-5-methoxypyridine-2-carboxamide of formula (I)

1 g of 4-(cyclopropylmethoxy)-N-(3,5-dichloro-1-oxidopyridin-4-yl)-5-methoxypyridine-2-carboxamide was dissolved by heating to reflux in 50 ml of ethyl acetate. The solution was cooled to room temperature, the precipitate filtered and dried to obtain crystal Form A of 4-(cyclopropylmethoxy)-N-(3,5-dichloro-1-oxidopyridin-4-yl)-5-methoxypyridine-2-carboxamide.

Example 5

Preparation of crystal Form A of 4-(cyclopropylmethoxy)-N-(3,5-dichloro-1-oxidopyridin-4-yl)-5-methoxypyridine-2-carboxamide of formula (I)

1 g of 4-(cyclopropylmethoxy)-N-(3,5-dichloro-1-oxidopyridin-4-yl)-5-methoxypyridine-2-carboxamide was dissolved by heating to reflux in 10 ml of tetrahydrofuran with 2 ml of water. The solution was cooled to room temperature, the precipitate filtered and dried to obtain crystal Form A of 4-(cyclopropylmethoxy)-N-(3,5-dichloro-1-oxidopyridin-4-yl)-5-methoxypyridine-2-carboxamide.

Example 6

Preparation of crystal Form A of 4-(cyclopropylmethoxy)-N-(3,5-dichloro-1-oxidopyridin-4-yl)-5-methoxypyridine-2-carboxamide of formula (I)

1 g of 4-(cyclopropylmethoxy)-N-(3,5-dichloro-1-oxidopyridin-4-yl)-5-methoxypyridine-2-carboxamide was dissolved by heating to reflux in 10 ml of ethanol plus 2 ml of water. The solution was cooled to room temperature, the precipitate filtered and dried to obtain crystal Form A of 4-(cyclopropylmethoxy)-N-(3,5-dichloro-1-oxidopyridin-4-yl)-5-methoxypyridine-2-carboxamide.

Example 7

Preparation of crystal Form D of 4-(cyclopropylmethoxy)-N-(3,5-dichloro-1-oxidopyridin-4-yl)-5-methoxypyridine-2-carboxamide of formula (I)

1 g of 4-(cyclopropylmethoxy)-N-(3,5-dichloro-1-oxidopyridin-4-yl)-5-methoxypyridine-2-carboxamide was dissolved by heating to reflux in 50 ml of methanol. The solution was cooled to room temperature, the precipitate filtered and dried to obtain form D of 4-(cyclopropylmethoxy)-N-(3,5-dichloro-1-oxidopyridin-4-yl)-5-methoxypyridine-2-carboxamide Example 8

Preparation of crystal Form D of 4-(cyclopropylmethoxy)-N-(3,5-dichloro-1-oxidopyridin-4-yl)-5-methoxypyridine-2-carboxamide of formula (I)

1 g of 4-(cyclopropylmethoxy)-N-(3,5-dichloro-1-oxidopyridin-4-yl)-5-methoxypyridine-2-carboxamide was dissolved by heating to reflux in 36 ml of ethanol. The solution was cooled to room temperature, the precipitate filtered and dried to obtain form D of 4-(cyclopropylmethoxy)-N-(3,5-dichloro-1-oxidopyridin-4-yl)-5-methoxypyridine-2-carboxamide Example 9

Preparation of crystal Form D of 4-(cyclopropylmethoxy)-N-(3,5-dichloro-1-oxidopyridin-4-yl)-5-methoxypyridine-2-carboxamide of formula (I)

1 g of 4-(cyclopropylmethoxy)-N-(3,5-dichloro-1-oxidopyridin-4-yl)-5-methoxypyridine-2-carboxamide was dissolved by heating to reflux in 20 ml of acetonitrile. The solution was cooled to room temperature, the precipitate filtered and dried to obtain form D of 4-(cyclopropylmethoxy)-N-(3,5-dichloro-1-oxidopyridin-4-yl)-5-methoxypyridine-2-carboxamide Example 10

Preparation of crystal Form D of 4-(cyclopropylmethoxy)-N-(3,5-dichloro-1-oxidopyridin-4-yl)-5-methoxypyridine-2-carboxamide of formula (I)

1 g of 4-(cyclopropylmethoxy)-N-(3,5-dichloro-1-oxidopyridin-4-yl)-5-methoxypyridine-2-carboxamide was dissolved by heating to reflux in 10 ml of acetonitrile plus 2 ml of water. The solution was cooled to room temperature, the precipitate filtered and dried to obtain form D of 4-(cyclopropylmethoxy)-N-(3,5-dichloro-1-oxidopyridin-4-yl)-5-methoxypyridine-2-carboxamide Example 11

Preparation of crystal Form H of 4-(cyclopropylmethoxy)-N-(3,5-dichloro-1-oxidopyridin-4-yl)-5-methoxypyridine-2-carboxamide of formula (I)

1 g of 4-(cyclopropylmethoxy)-N-(3,5-dichloro-1-oxidopyridin-4-yl)-5-methoxypyridine-2-carboxamide was dissolved by heating to reflux in 170 ml of acetone. The solution was cooled to room temperature, the precipitate filtered and dried to obtain form D of 4-(cyclopropylmethoxy)-N-(3,5-dichloro-1-oxidopyridin-4-yl)-5-methoxypyridine-2-carboxamide Example 12

Preparation of crystal Form G of 4-(cyclopropylmethoxy)-N-(3,5-dichloro-1-oxidopyridin-4-yl)-5-methoxypyridine-2-carboxamide of formula (I)

1 g of 4-(cyclopropylmethoxy)-N-(3,5-dichloro-1-oxidopyridin-4-yl)-5-methoxypyridine-2-carboxamide was dissolved by heating to reflux in 1.5 ml of dimethylsulfoxide. The solution was cooled to room temperature, the precipitate filtered and dried to obtain form D of 4-(cyclopropylmethoxy)-N-(3,5-dichloro-1-oxidopyridin-4-yl)-5-methoxypyridine-2-carboxamide

EXPERIMENTALS

Said Crystal Forms A to I according to the invention were characterized by one or several physical methods such as X-ray Powder Diffraction, Thermo-Gravimetric Analysis, Water-Activity isotherm measurement, as shown below.

X-Ray Powder Diffraction (XRPD)

High-resolution diagrams are recorded at ambient conditions on a PANalytical X'Pert Pro MPD powder diffractometer using the Bragg-Brentano (vertical θ-2θ configuration) parafocusing geometry coupled with a X'Celerator detector. A sealed copper anode X-ray tube is used, running at 45 kV and 40 mA levels. An incident beam monochromator (Johansson type: a symmetrically cut curved germanium (111) crystal) produces pure Cu $K\alpha_1$ radiation ($\lambda$=1.54060 Å). A thin layer of the product is deposited on a single-crystal silicon wafer, cut out according to Si (510) crystallographic orientation that, by systematic extinction, impedes any Bragg reflection. In order to bring more crystallites into the diffraction position and thus reduce the influence of particle statistics on the measurements, a sample spinner is used. The spinner rotation speed is set at 1 revolution per second. The angular range extends from 2 to 50° in 2θ, with a 0.02° step size in 2θ. A variable counting time from 100 to 2500 seconds per step was used.

The so obtained XRPD diagrams for samples of Crystal Forms A, B, and D to I are shown in FIG. 1, 4, 6, 9, 12 to 15.

XRPD analyses are carried out on a Siemens-Bruker D5000 Matic powder diffractometer using the Bragg-Brentano (vertical θ-2θ configuration) parafocusing geometry. A thin layer of the product is deposited on a single-crystalline silicon wafer, cut out according to Si(510) crystallographic orientation that, by systematic extinction, impedes any Bragg reflection. A sealed cobalt anode X-ray tube running at 40 kV and 30 mA levels is used. Two lines are typically emitted: $CoK\alpha_1$ ($\lambda$=1.7890 Å) and $CoK\alpha_2$ ($\lambda$=1.7929 Å). An Iron β-filter, placed between the detector and specimen, does not altogether eliminate CoKβ ($\lambda$=1.6208 Å) radiation, which still contributes about 1% of the diffracted beam at the detector (manufacturer's data). The primary beam passes through a parallel plate collimator (0.2 mm Soller slits), then through a divergence slit (0.2 mm). A Braun 50 M multicanal linear detector completes the setup. It has a 10°-wide detection window in angle 2θ.

Figure 5:
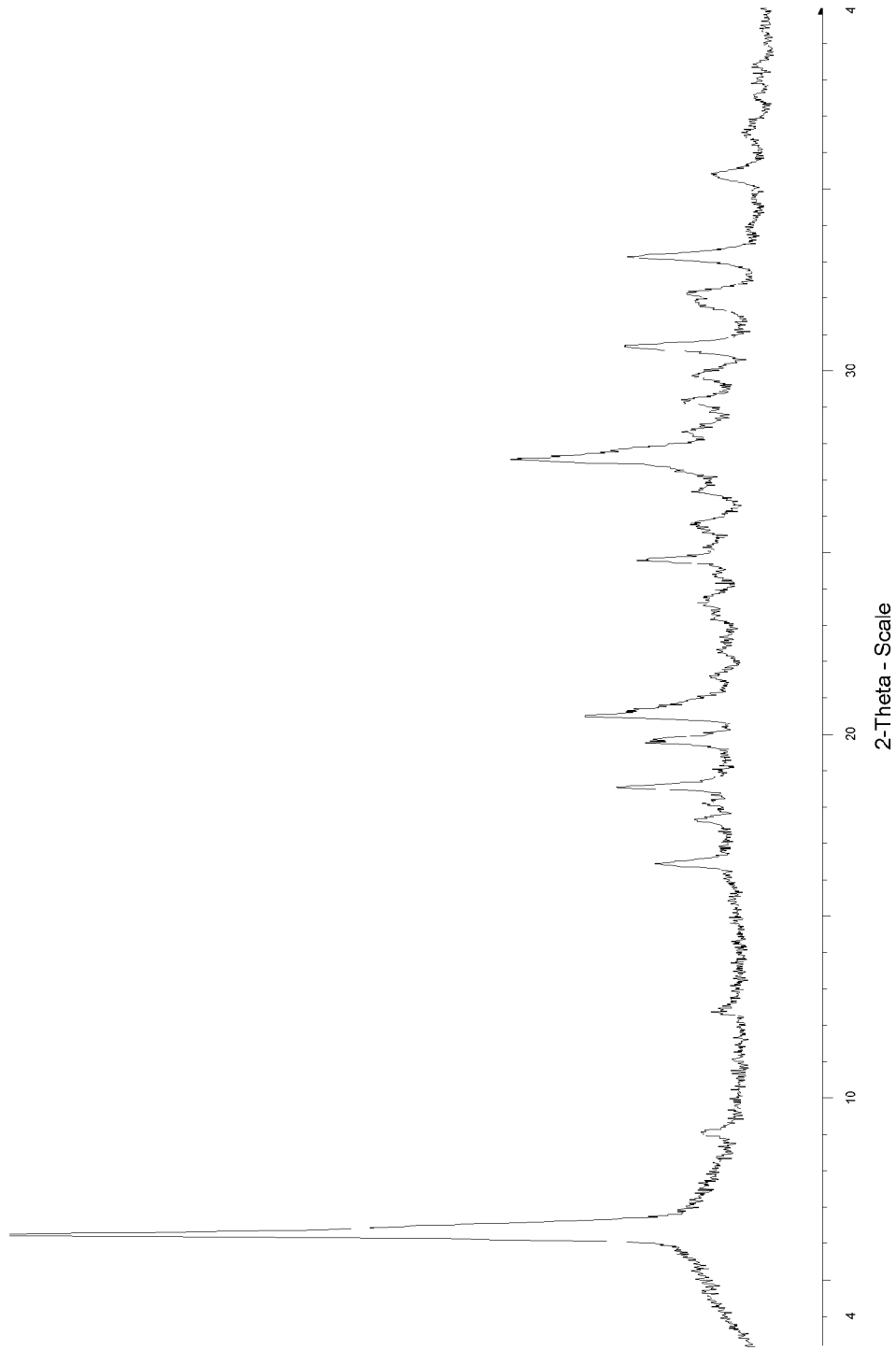
FIG. 5 is an X-ray Powder Diffractogram (λCo) of Crystal Form C of 4-(cyclopropylmethoxy)-N-(3,5-dichloro-1-oxidopyridin-4-yl)-5-methoxypyridine-2-carboxamide of the present invention.
Figure 6:
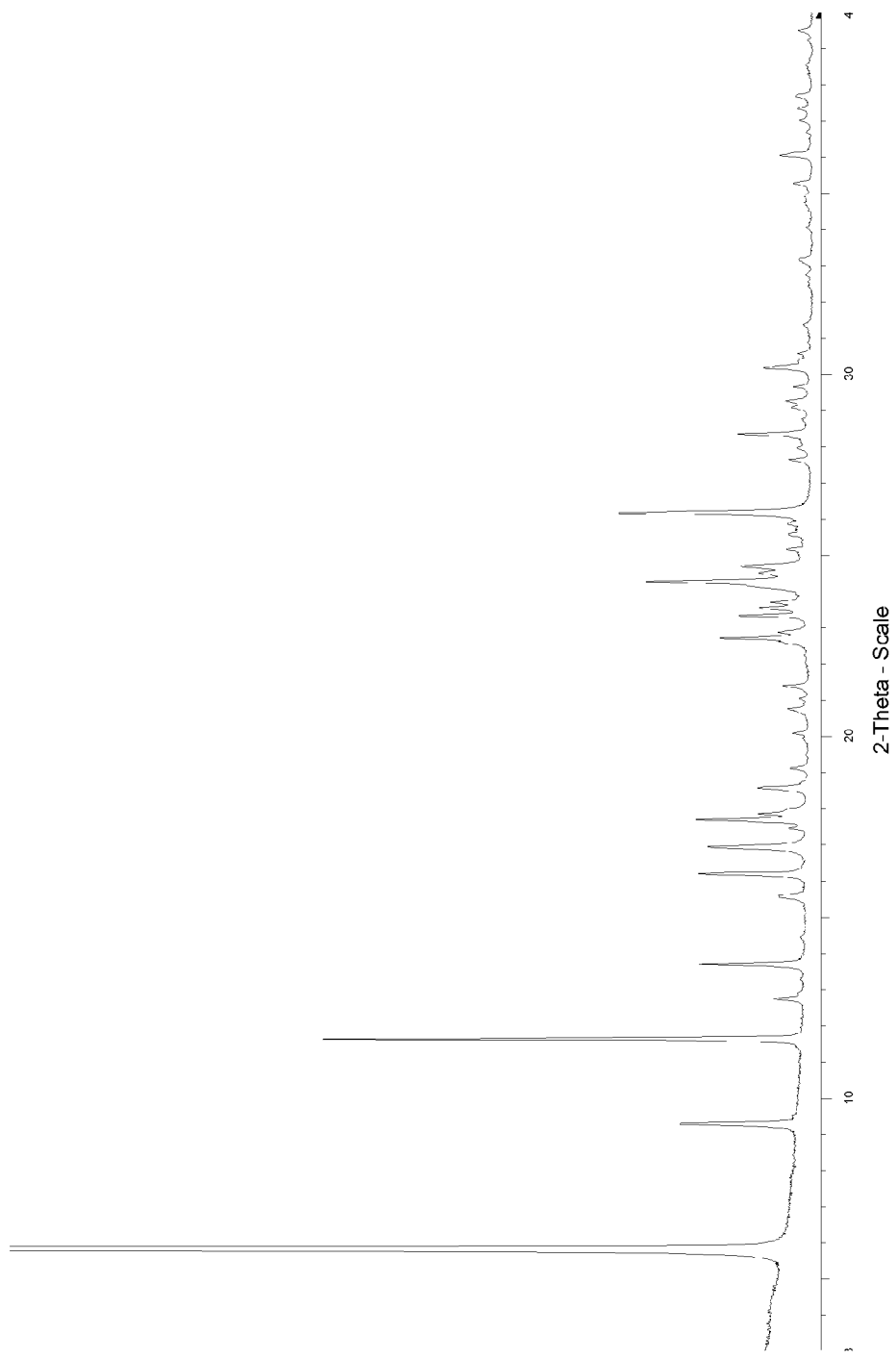
FIG. 6 is an X-ray Powder Diffractogram (λCu) of Crystal Form D of 4-(cyclopropylmethoxy)-N-(3,5-dichloro-1-oxidopyridin-4-yl)-5-methoxypyridine-2-carboxamide of the present invention.

The so obtained XRPD diagram for sample of Crystal Form C is shown in FIG. 5.

Thermo-Gravimetric Analysis (TGA)

Analyses are carried out on a T.A. instruments TGAQ500 analyzer. Mass calibration is performed with 10 and 100 mg certified masses and the instrument is temperature-calibrated with alumel and nickel standards (Curie points of respectively 154° C. and 354° C.). Samples are exposed to a constant nitrogen stream of 60 mL/min and temperature ranges from 20° C. to 250° C. at a 5° C./min rate. The quantity of product lies between 2 and 5 mg. The powder is deposited in an open aluminum sample pan, which is itself placed in a platinum pan.

The so obtained TGA diagrams for samples of Crystal Forms A, D and E are shown in FIGS. 2, 7 and 10.

Water-Activity Isotherm (DVS)

All experiments are performed on a DVS-1 automated gravimetric vapor sorption analyser (Surface Measurement Systems Ltd., London, UK). The DVS-1 measures the uptake and loss of vapor gravimetrically using a Cahn D200 recording ultra-microbalance with a mass resolution of ±0.1 µg. A controlled relative humidity is generated by mixing different proportions of dry and water saturated carrier gas streams (monitored by mass flow controllers). The temperature is maintained constant, ±0.1° C., by enclosing the entire system in a temperature-controlled incubator. A sample size between 4 and 10 mg is used. Prior to being exposed to any water vapor the samples are dried at 0% RH to remove any surface water present and establish a dry, baseline mass. Next, the samples are exposed to an increasing relative humidity raised by a step of 5% RH from 0% to 90% RH. At each stage, the sample mass is allowed to reach equilibrium before the relative humidity is increased or decreased (considering that equilibrium is established when dm/dt ratio (m=mass; t=time) does not exceed the value of $3.3 \cdot 10^{-4}$ mg/s (during 30 minutes). If equilibrium state is not reached, the change in relative humidity takes place automatically after 600 minutes. From the complete moisture sorption and desorption profile an isotherm is calculated using the DVS Advanced Analysis Suite v3.6. All experiments are performed at 25° C.

Figure 11:
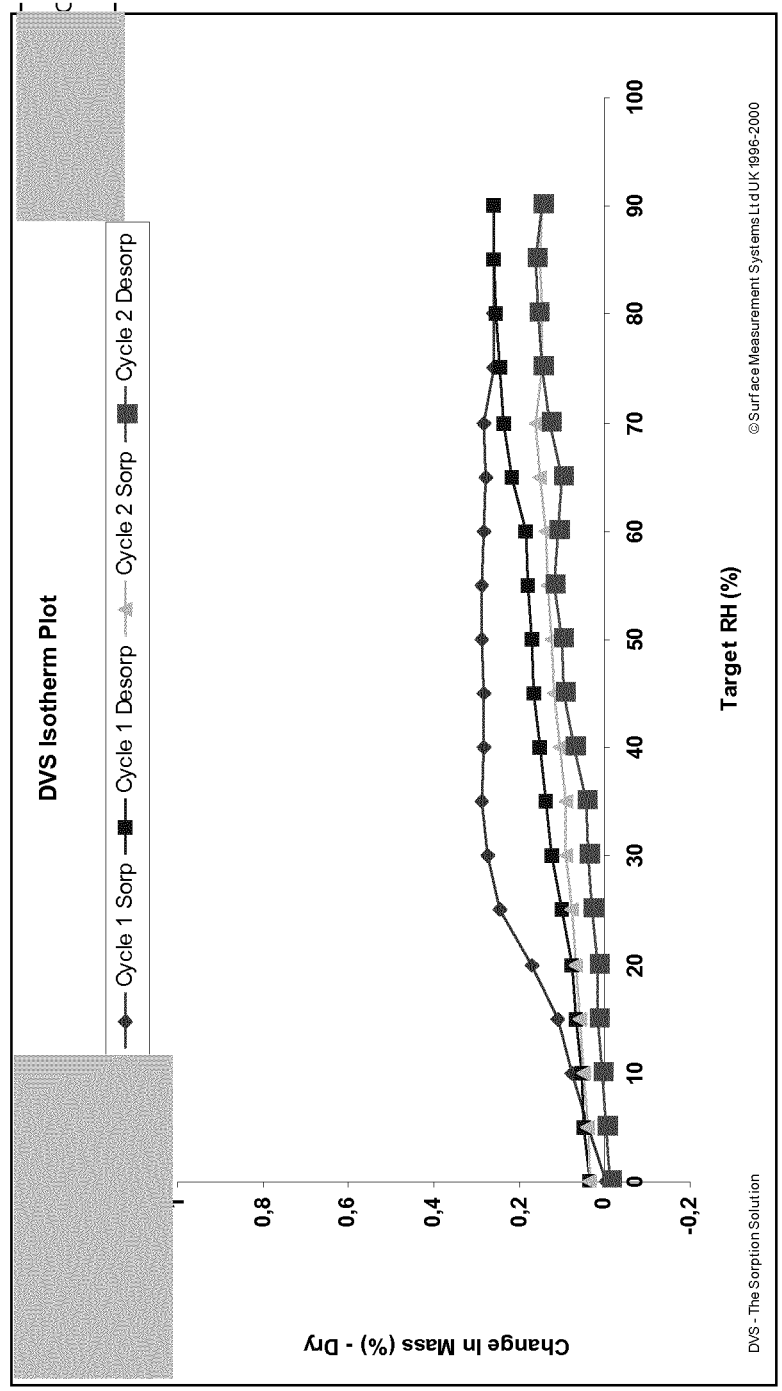
FIG. 11 shows water sorption/desorption isotherms recorded at 25° C. of Crystal Form E of 4-(cyclopropylmethoxy)-N-(3,5-dichloro-1-oxidopyridin-4-yl)-5-methoxypyridine-2-carboxamide of the present invention.

The so obtained DVS diagrams for samples of Crystal Forms A, D and E are shown in FIGS. 3, 8 and 11.

The invention claimed is:

1. A process for the preparation of Crystal Form A of 4-(cyclopropylmethoxy)-N-(3,5-dichloro-1-oxidopyridin-4-yl)-5-methoxypyridine-2-carboxamide of formula (I)

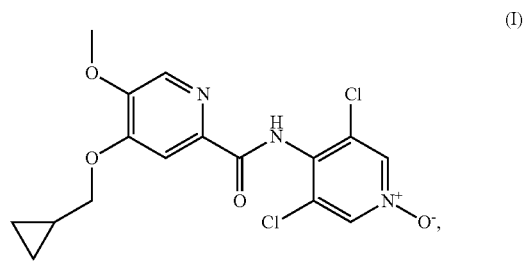 [SMILES: COc1cnc(C(=O)Nc2c(Cl)c[n+]([O-])cc2Cl)cc1OCC1CC1]

having an X-ray (λCu) powder diffraction pattern with main peaks at about 9.5, 10.9, 11.7, 13.3, 13.9, 14.9, 16.1, 17.6, 18.6, 19.2±0.2 degrees 2-theta, the process comprising heating 4-(cyclopropylmethoxy)-N-(3,5-dichloro-1-oxidopyridin-4-yl)-5-methoxypyridine-2-carboxamide in a solvent selected from the group consisting of propanol, isopropanol, toluene, ethyl acetate, a mixture of tetrahydrofuran and water, and a mixture of ethanol and water to provide a solution, and cooling the solution to induce crystallization.

2. The process according to claim 1 wherein the process further comprises filtration and drying.

3. A crystal form of 4-(cyclopropylmethoxy)-N-(3,5-dichloro-1-oxidopyridin-4-yl)-5-methoxypyridine-2-carboxamide of formula (I):

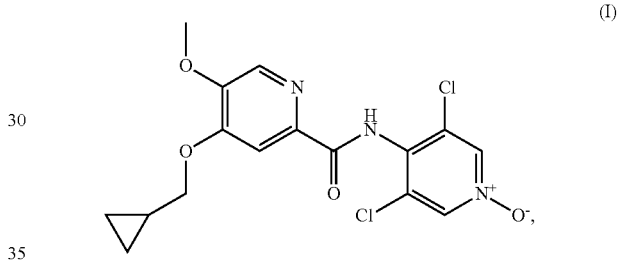

which is
crystal Form A, having an X-ray (λCu) powder diffraction pattern with main peaks at about 9.5, 10.9, 11.7, 13.3, 13.9, 14.9, 16.1, 17.6, 18.6, 19.2±0.2 degrees 2-theta.

4. A pharmaceutical composition comprising the crystal form of 4-(cyclopropylmethoxy)-N-(3,5-dichloro-1-oxidopyridin-4-yl)-5-methoxypyridine-2-carboxamide of formula (I) according to claim 3, and at least one pharmaceutically acceptable excipient.

5. A method of treating Alzheimer's disease or Parkinson's disease in a patient in need thereof, comprising administering to the patient a therapeutically effective amount of the crystal form of 4-(cyclopropylmethoxy)-N-(3,5-dichloro-1-oxidopyridin-4-yl)-5-methoxypyridine-2-carboxamide of formula (I) according to claim 3.

* * * * *